United States Patent
Sakamoto

[11] Patent Number: 6,095,972
[45] Date of Patent: Aug. 1, 2000

[54] LARYNGOSCOPE

[76] Inventor: Carl Kaoru Sakamoto, 44 Robb Farm Rd., North Oaks, Minn. 55127

[21] Appl. No.: 09/216,224

[22] Filed: Dec. 18, 1998

[51] Int. Cl.[7] ................................................. A61B 1/267
[52] U.S. Cl. ...................... 600/190; 600/194; 600/196; 600/197; 600/199
[58] Field of Search ................................. 600/120, 185, 600/190, 191, 192, 193, 194, 195, 196, 197, 199

[56] References Cited

U.S. PATENT DOCUMENTS

| | | |
|---|---|---|
| 4,314,551 | 2/1982 | Kadell . |
| 4,360,008 | 11/1982 | Corazzelli, Jr. . |
| 4,573,451 | 3/1986 | Bauman . |
| 4,827,910 | 5/1989 | Mathews, III . |
| 5,498,231 | 3/1996 | Franicevic .............................. 600/190 |
| 5,584,795 | 12/1996 | Valenti . |
| 5,984,863 | 11/1999 | Ansari ..................................... 600/185 |

FOREIGN PATENT DOCUMENTS

WO 98/19589  5/1998  WIPO .

Primary Examiner—Linda C. M. Dvorak
Assistant Examiner—Brad C. Blaise
Attorney, Agent, or Firm—Scott V. Lundberg

[57] ABSTRACT

This laryngoscope has a blade whose height is tapered shorter at the end that is connected to the handle and whose other end has two pivotally connected tips. The tips are manually operated on by a mechanism that is controlled by the operator's thumb. When the blade is in place and the tips are activated, one tip displaces the epiglottis anteriorly and the other tip displaces the posterior wall of laryngopharynx posteriorly thereby exposing the aditus of larynx for intubation. In addition, the width of the blade tips flare out beyond the width of the blade.

22 Claims, 17 Drawing Sheets

LARYNGOSCOPE

CROSS-REFERENCE TO RELATED APPLICATIONS

Not Applicable.

STATEMENT REGARDING FEDERALLY SPONSORED RESEARCH

Not Applicable.

BACKGROUND OF INVENTION

The present invention relates to the improvement of a laryngoscope. A laryngoscope is a device that is used to position an endotrachel tube in a patient's trachea. The primary purpose of a laryngoscope is to expose the aditus of larynx thereby allowing an endotracheal tube to be inserted past the vocal cords into the patient's trachea. The insertion of an endotracheal tube provides an airway for ventilation and prevents foreign substances from entering the patent's trachea and lungs.

Laryngoscopes generally have three main parts, a handle, a blade and a light source. A good example of this can be found in U.S. Pat. No. 2,433,705 (Palmeter). The operator grasps the handle and inserts the blade through the patient's oral cavity into the patient's laryngopharynx. The blade displaces the tongue and throat tissue exposing the aditus of larynx. Laryngoscope blades come in different sizes and curvatures and are commonly detachable from the handle. An example of a laryngoscope having a substantially straight blade is the "Jackson" laryngoscope blade. The "Miller Blade," commonly used in the art, is an example of a blade that is substantially straight with a curved tip. A blade that is curved through out its length can be seen in U.S. Pat. No. 2,354,471 (MacIntosh).

Generally, traditional laryngoscopes with straight or curved blades do the job effectively. There are, however, patients in which traditional laryngoscopes do not work effectively. This may be due to the patient having congenital deformities such as, a short "bull" neck, protruding or carious upper incisor teeth, over development of the tongue, a short ridged epiglottis, a narrow oral cavity or pathological conditions such as cervical arthrosis or mandibular anchylosis. When an emergency situation occurs, these patients are at great risk because the operator may have just seconds to expose the vocal cords to establish an airway or risk losing the patient.

Inventors have tried to address this situation but have been unable to come up with a device that is effective and that has received wide acceptance from the medical community. Blades that are capable of changing curvature like that found in U.S. Pat. No. 4,573,451 (Bauman) and U.S. Pat. No. 5,584,795 (Valenti) have been tried. So has a blade that moves on a pivot connection, U.S. Pat. No. 4,573,451 (Kadell). These blades, however, are difficult to use in emergency situations and are not effective on all patients. Corrazzi Jr., in U.S. Pat. No. 4,360,008 invented a laryngoscope that has a blade with a movable distal tip. The movable tip is used to anteriorly displace the soft tissue of the laryngeal area, such as the epiglottis, but may only result in posterior displacement of the entire blade. Although, the posterior displacement could be compensated by rotation of the blade at the proximal base, the rotation may, however, be prohibited or restricted by the patient's teeth.

Another problem with Corrazzi's invention is the placement of the actuating lever that moves the distal tip. This problem is also seen in Kadell's invention. In both inventions the activation lever is projected alongside the handle. When inserting a laryngoscope the operator must tightly grasp the handle. The placement of the activating lever as disclosed in the Corrazzi patent and Kadell patent would impede the operators ability to grasp of the handle and may result in the inadvertent engagement of the respective inventions during insertion. This could impede proper positioning of the laryngoscope blade and may result in injury to the patient.

In addition, the Corrazzi invention as disclosed has another potential problem. If the biasing spring fails the single tip may remain in the activated state. This could interfere with the removal of the blade, inhibit repositioning of the blade and may even result in injury to the patient.

The need for a laryngoscope that will expose the aditus of larynx in those patients in which traditional laryngoscopes do not work in a simple manner has been long felt. My present invention satisfies those needs.

BRIEF SUMMARY OF INVENTION

The laryngoscope I have invented overcomes the foregoing problems. My laryngoscope has two tips at the end of a straight or curved laryngoscope blade. The blade tips have the ability to pivot away from each other when activated on by the operator. When the laryngoscope blade is inserted in the patient's laryngopharynx and activated the patient's throat tissue is spread apart by the blade tips. More specifically, one tip displaces the epiglottis anteriorly and the other tip displaces the posterior wall of the laryngopharynx thereby allowing greater exposure to the aditus of larynx for easier insertion of an endotracheal tube. Moreover, my laryngoscope avoids posterior displacement of the blade during activation because anteriorly directed pressure asserted by the upper blade tip is stabilized by simultaneous posteriorly directed pressure asserted by the lower blade tip.

My laryngoscope also has a blade that varies in height. The height of the blade on the end that connects to the handle is tapered shorter relative to the height of the main portion of the blade. This shortening of the height of the blade, a the proximal end, gives the operator greater maneuverability and a better angle to work with because it provides more room between the blade and the patient's upper teeth.

The pivoting tips of my laryngoscope are activated by a mechanism that is controlled by the operators thumb. The activating member is placed in a position that allows the operator to tightly grasp the handle, feels natural to engage and is unlikely to be activated during insertion of the blade. Moreover, the mechanism allows the operator to control the amount of pressure exerted thereby lessening the chance of damaging the patient's throat tissue. In addition, it is a direct mechanism that allows the operator to manually disengage the tips if its biasing spring fails.

Another, feature of my invention is that the width of the distal aspects of the blade tips are flared out beyond the width of the blade. This design gives the tips more surface area to spread apart a patient's throat tissue and to stabilize the epiglottis while displacing it anteriorly. In addition, the widening of the blade at its distal end allows for the width of the rest of the blade to be narrower which enhances the maneuverability of laryngoscope and provides the operator with greater exposure of the aditus of larynx/vocal cords.

I have invented a laryngoscope that is simple and efficient to use in emergency situations where present laryngoscopes would be ineffective.

BRIEF DESCRIPTION OF THE SEVERAL VIEWS OF THE DRAWINGS

A complete understanding of my invention may be obtained by considering my accompanying disclosure in conjunction with the following drawings.

DETAILED DESCRIPTION OF THE INVENTION

Figure 1:
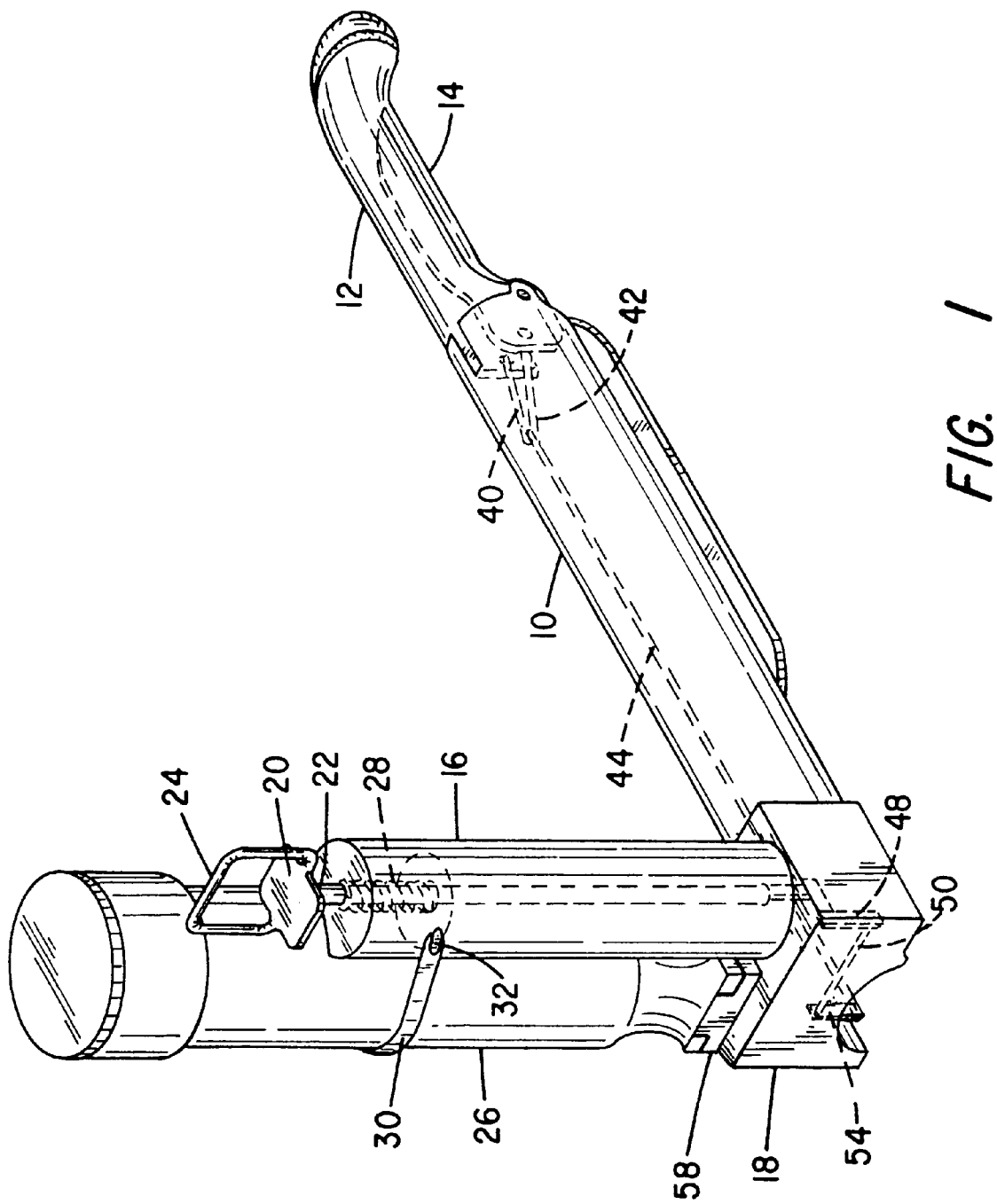
FIG. 1 is a perspective view of the preferred embodiment of the invention in connection with a standard laryngoscope handle.
Figure 2:
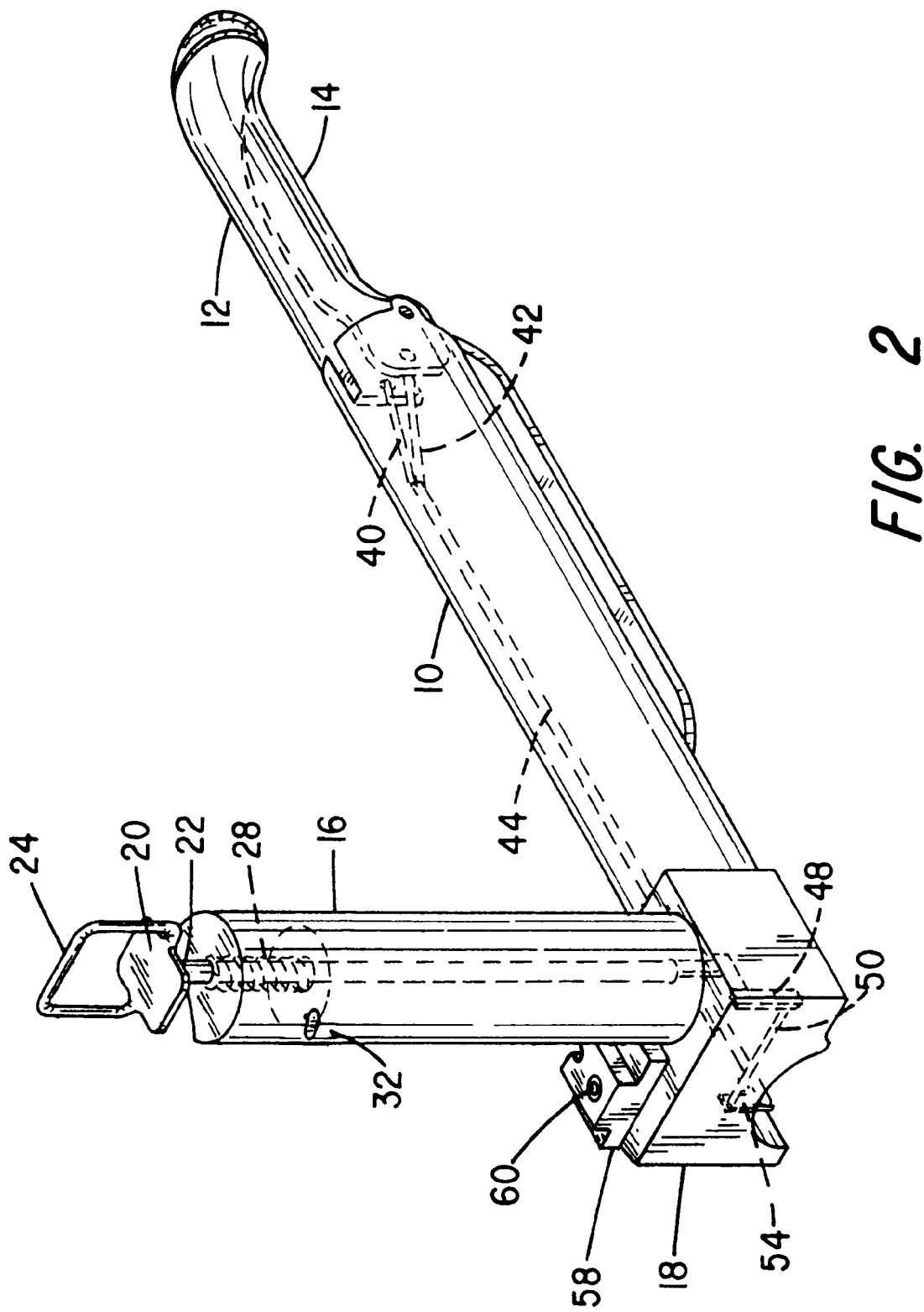
FIG. 2 is a perspective view of the preferred embodiment of the invention.
Figure 23:
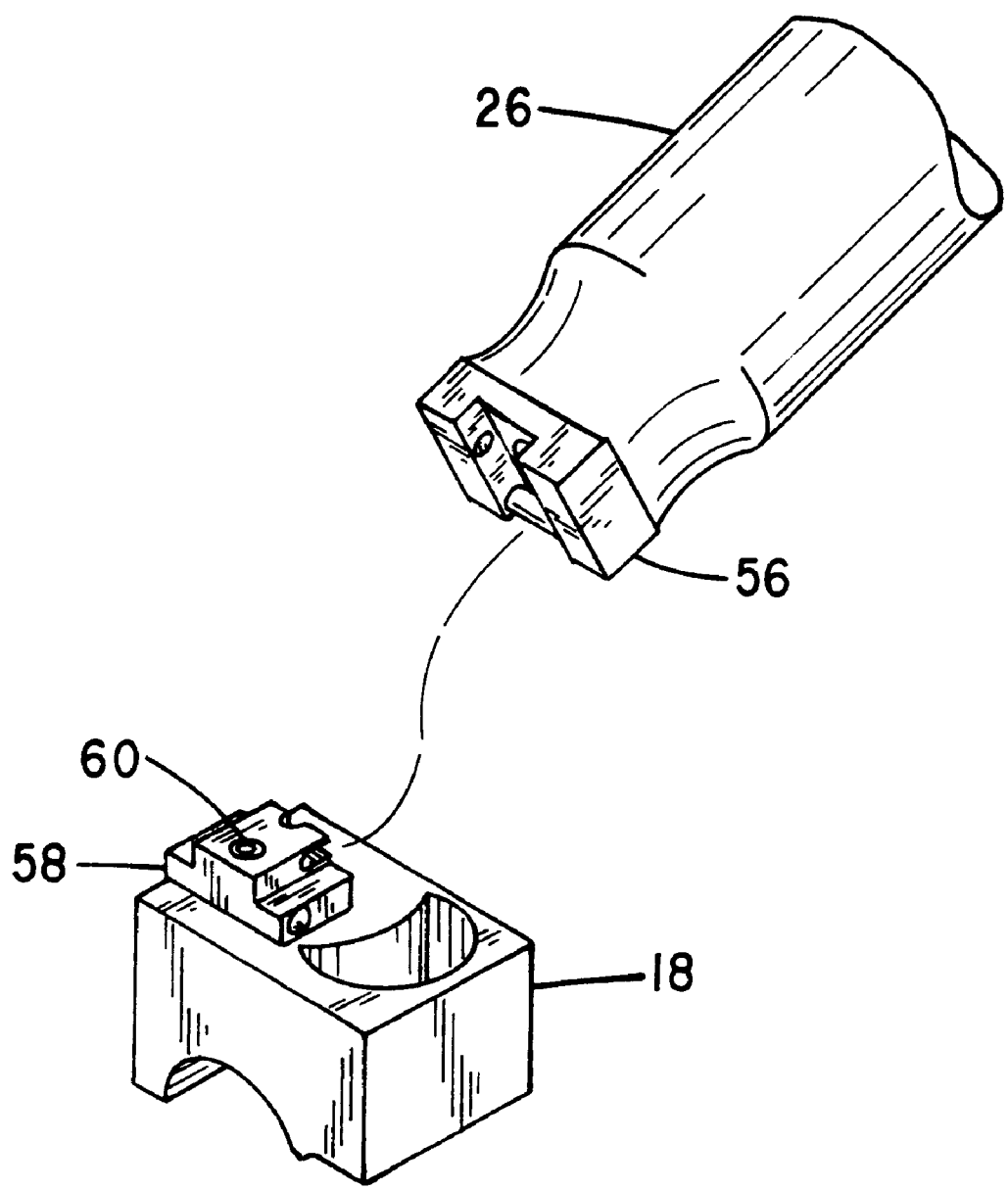
FIG. 23 is a perspective view of the bade body base and standard handle showing how they are connected.
Figure 24:
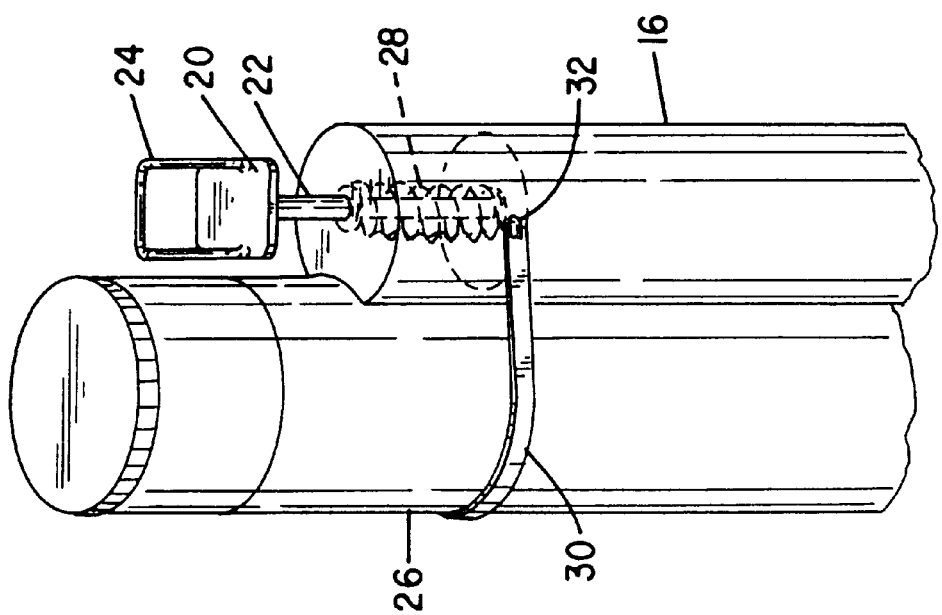
FIG. 24 is a back elevational view of the handle, thumb push rod housing, thumb plunger and biasing spring showing how they relate to each other.

My invention is illustrated in FIG. 1. The blade 10 of the laryngoscope can either be detachably connected to a standard laryngoscope handle 26 or be solidly connected to a handle 26. My preferred embodiment calls for the blade 10 to be detachably connected to the handle 26 as illustrated in FIG. 2. This allows for ease of cleaning of the blade 10 after it has been used. FIG. 23 illustrates how the blade 10 is detachably connected to a standard laryngoscope handle 26. The handle connector 56 slides into and locks onto the base connector 58. This connection is standard in the art and is of the type disclosed in Palmeter U.S. Pat. No. 2,433,705. Once the handle 26 is locked onto the base connector 58, the thumb push rod guide 16 is secured to the handle 26 with a stabilizing strap 30 as illustrated in FIG. 24. The stabilizing strap 30 is designed to engage a pair of stabilizing knobs 32 that are attached to the thumb push rod guide 16.

Figure 26:
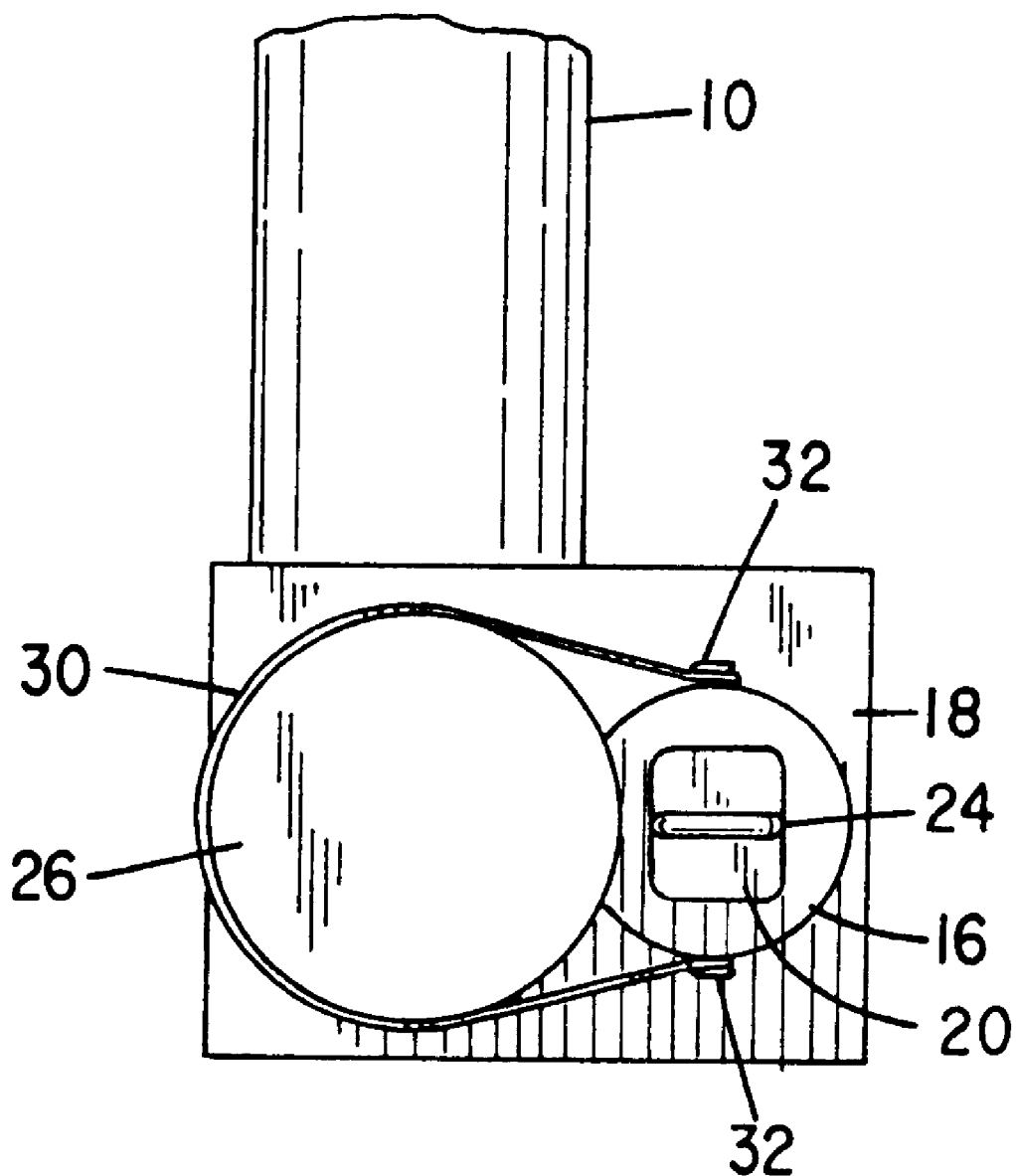
FIG. 26 is a top-elevational view of the handle and thumb push rod housing showing they are connected to each other.

The thumb push rod guide 16 is shaped to receive the handle 26. Both of these features are illustrated in FIG. 26.

Figure 3:
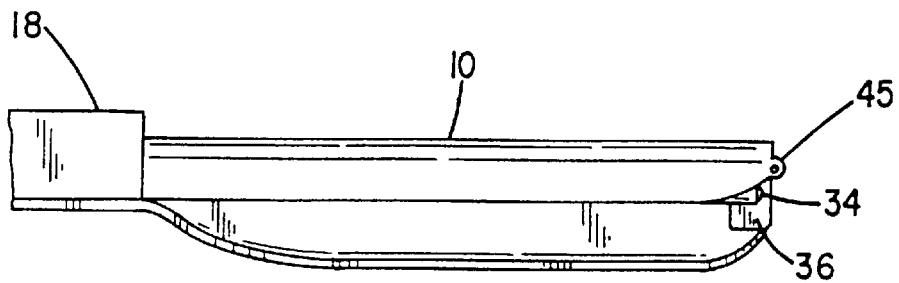
FIG. 3 is a right-side elevational view of the laryngoscope blade without the blade tips attached.

My laryngoscope also has a light source 34, illustrated in FIG. 3. The light source 34 may be part of an electric circuit like that disclosed in Palmeter U.S. Pat. No. 2,433,705 with the light being activated when the handle 26 is connected to the blade body base 18 through a light source conduit 60 as illustrated in FIG. 23. The light source 34 may also be part of a fiber optic circuit common in the art. Since, the electrical circuit and the fiber optic circuit are known in the art and they are not germane to my invention, the details of their construction are not included in my disclosure.

Figure 4:
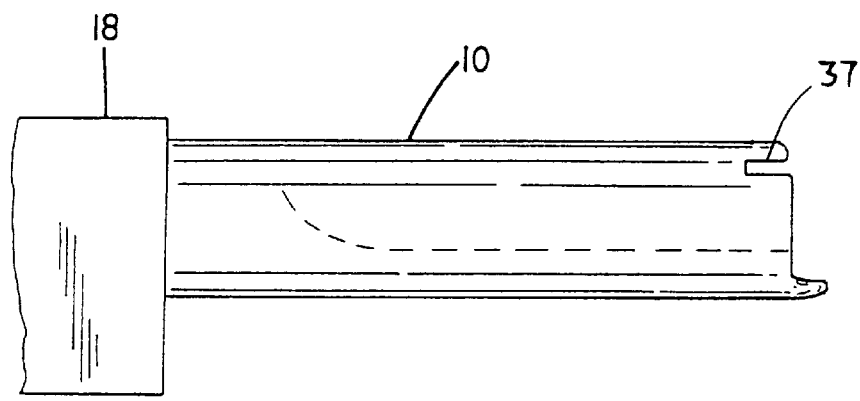
FIG. 4 is a top-elevational view of the laryngoscope blade without the blade tips attached.
Figure 6:
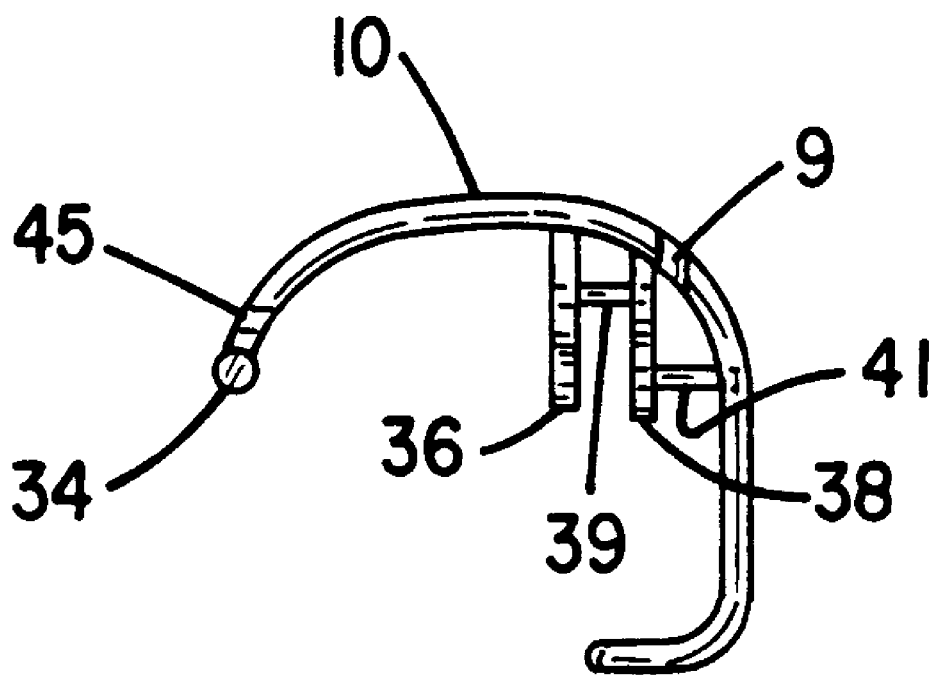
FIG. 6 is a front-side elevational view of the laryngoscope blade without the blade tips attached.
Figure 11:
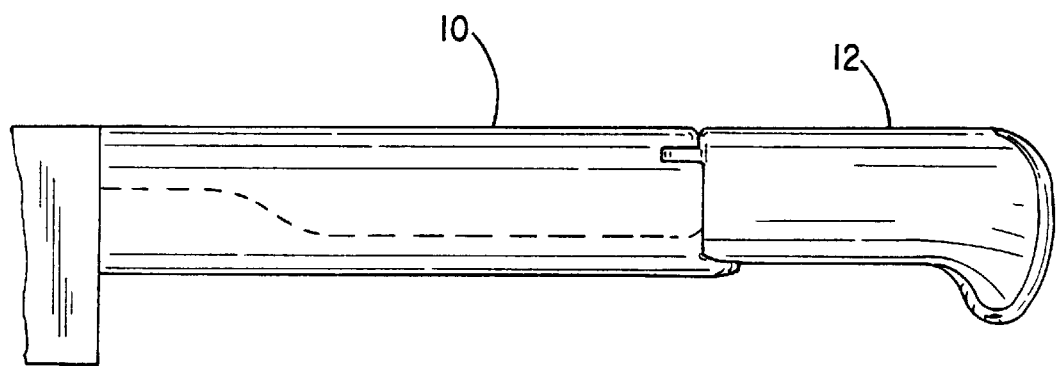
FIG. 11 is a a top-elevational view of the laryngoscope blade with the upper blade attached.
Figure 27:
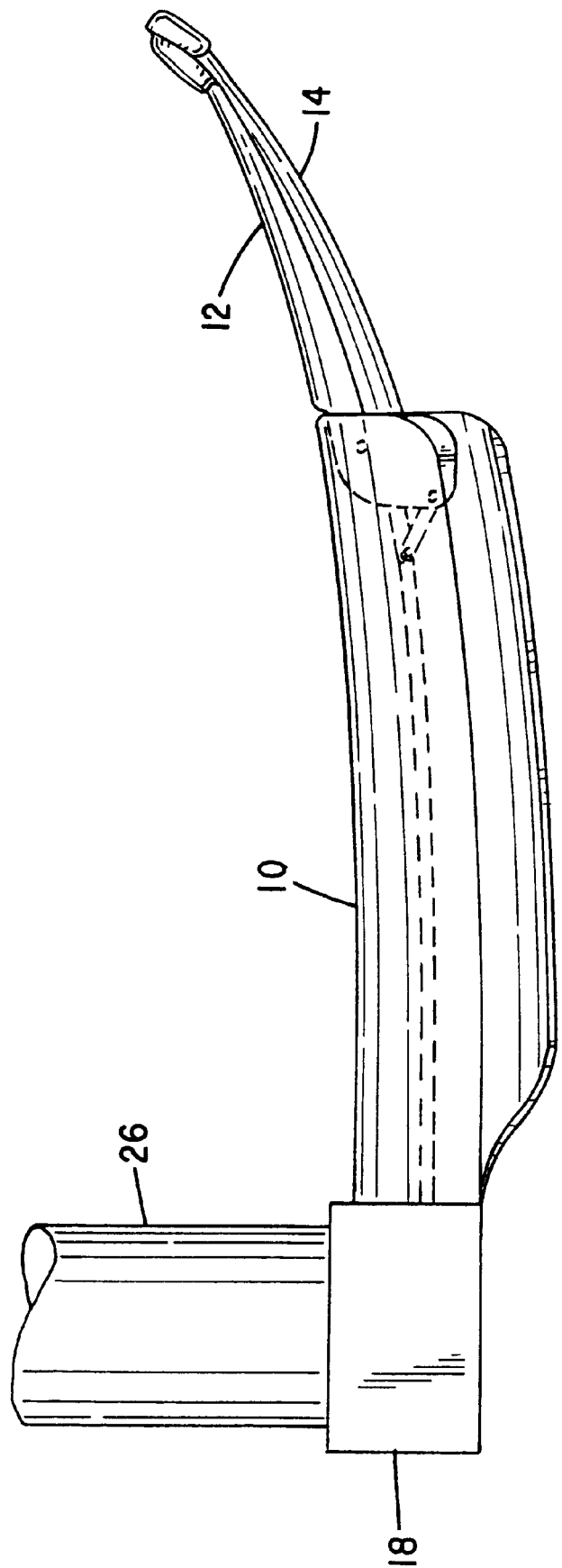
FIG. 27 is a perspective view the invention with a curved blade.

The laryngoscope blade 10 of my invention may either be straight as illustrated in FIG. 2 or curved as illustrated in FIG. 27. The proximal end of the blade 10 is connected to the blade body base 18 as illustrated in FIG. 3. An upper tip flange 38 and a lower tip flange 36 are connected to the distal end of the blade 10 as illustrated in FIG. 6. The distal end of the blade 10 also has a slot 37 cut out to allow for the upper blade 12 to be extended without obstruction as illustrated in FIGS. 4 and 11.

The blade 10 is designed to provide the operator with a good visual channel 55 when the blade 10 is in use. The visual channel 55 is formed by an upper plate 49, a lower plate 51 and an edge plate 47. The edge plate 47 extends between a side of the upper plate 49 and the lower plate 51, as illustrated in FIG. 6. The height of the edge plate 47 defines the height of the blade 10.

Figure 5:
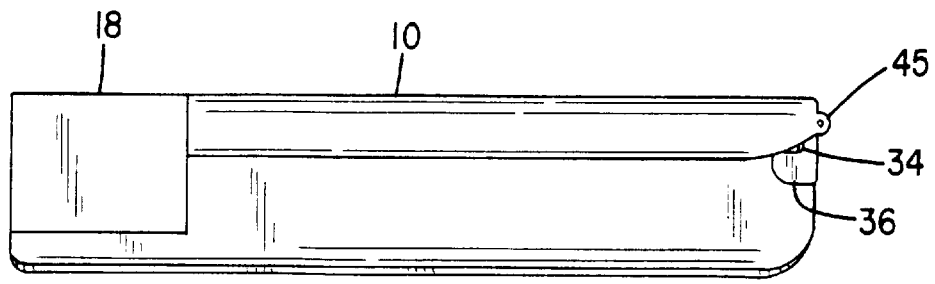
FIG. 5 is a right-side elevational view of the laryngoscope blade with the blade's height being the same throughout the length of the blade.
Figure 12:
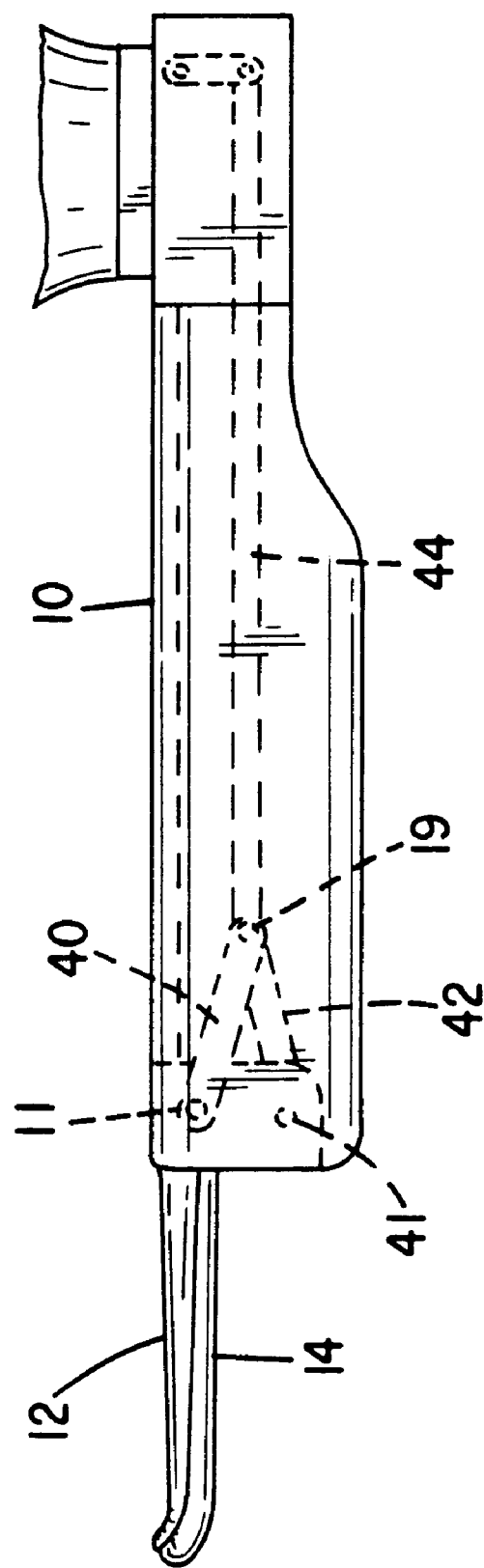
FIG. 12 is a left-side elevational view of the laryngoscope blade with upper and lower blades attached.

The shape of the blade 10 can extend the entire length of the blade 10 as illustrated in FIG. 5, the blade 10 may have a cutout portion 53 that shortens the height of the blade 10 at its proximal end as illustrated in FIG. 3. Shortening of the height of the blade 10 at the proximal end gives the operator greater area to work with when the blade 10 is being positioned in a patient's oral cavity A and laryngopharynx B. It also provides greater distance between the bottom proximal end of the blade and the patient's upper teeth. This gives the operator a better angle to anteriorly place the distal aspect of the blade 10. The right lateral side of the blade 10 is open as illustrated in FIG. 3. The left lateral side of the blade 10, which is the edge portion 47 of the blade 10, is solid as illustrated in FIG. 12. This provides an edge to displace the patient's tongue C.

Figure 7:
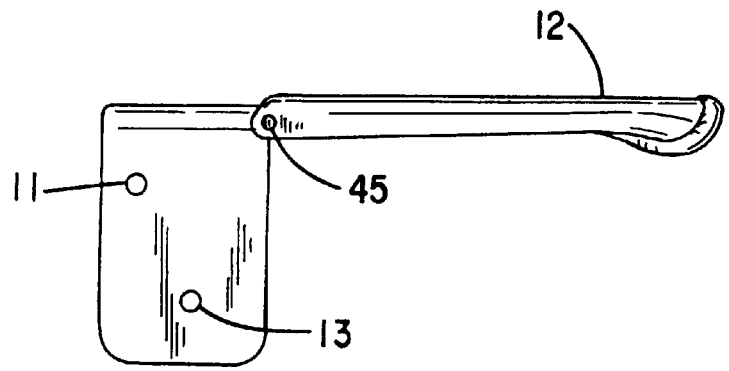
FIG. 7 is a right-side elevational view of the upper blade tip.
Figure 8:
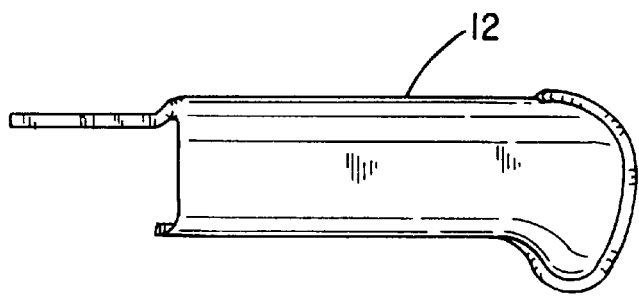
FIG. 8 is a top-elevational view of the upper blade tip.
Figure 9:
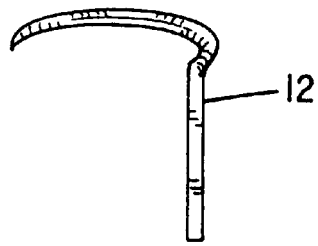
FIG. 9 is a front-side elevational view of the upper tip.
Figure 10:
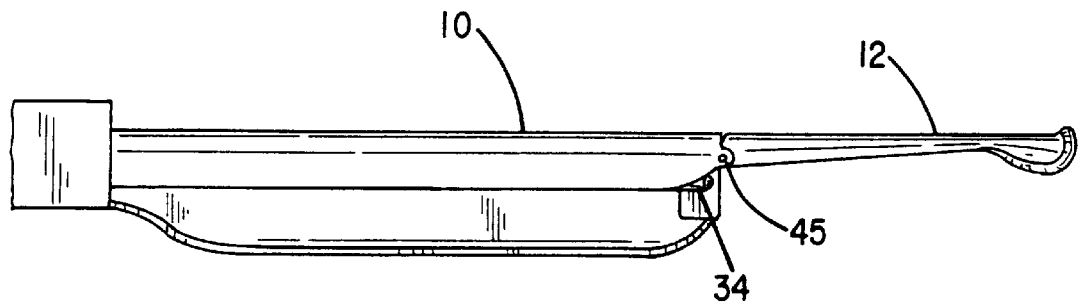
FIG. 10 is a right-side elevational view of the laryngoscope blade with the upper blade attached.
Figure 13:
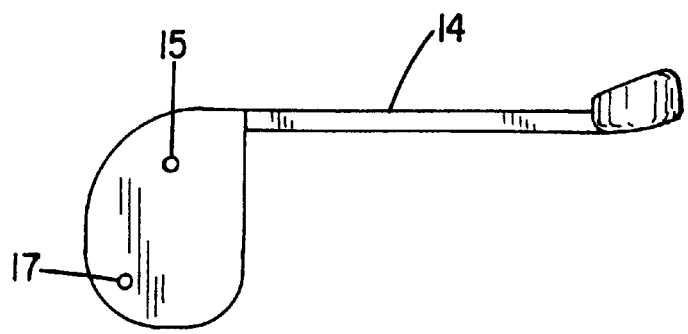
FIG. 13 is a right-side elevational view of the lower blade tip.
Figure 14:
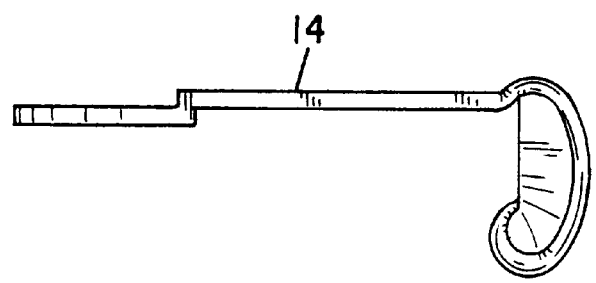
FIG. 14 is a top-elevational view of the lower blade tip.
Figure 15:
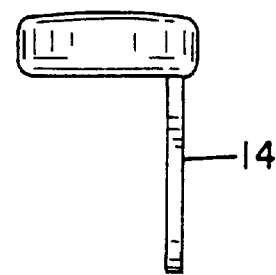
FIG. 15 is a front-side elevational view of the bottom blade tip.
Figure 18:
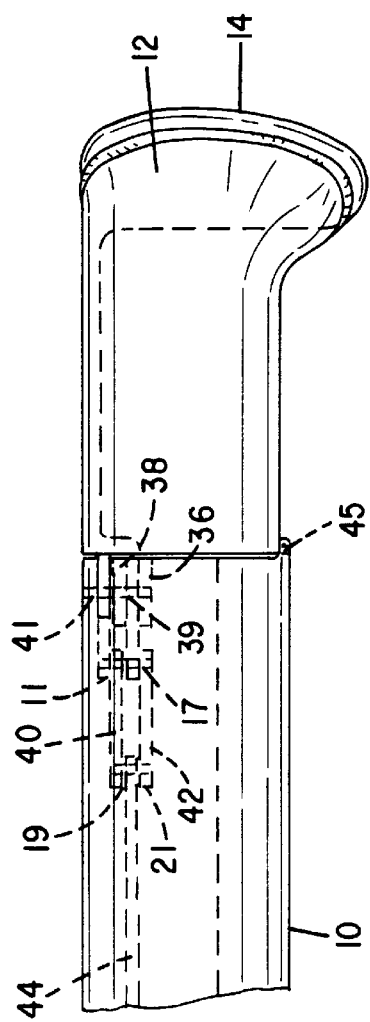
FIG. 18 is a top-cross-sectional view of the laryngoscope blade with both the upper and lower blade tips attached showing pivot connections.
Figure 19:
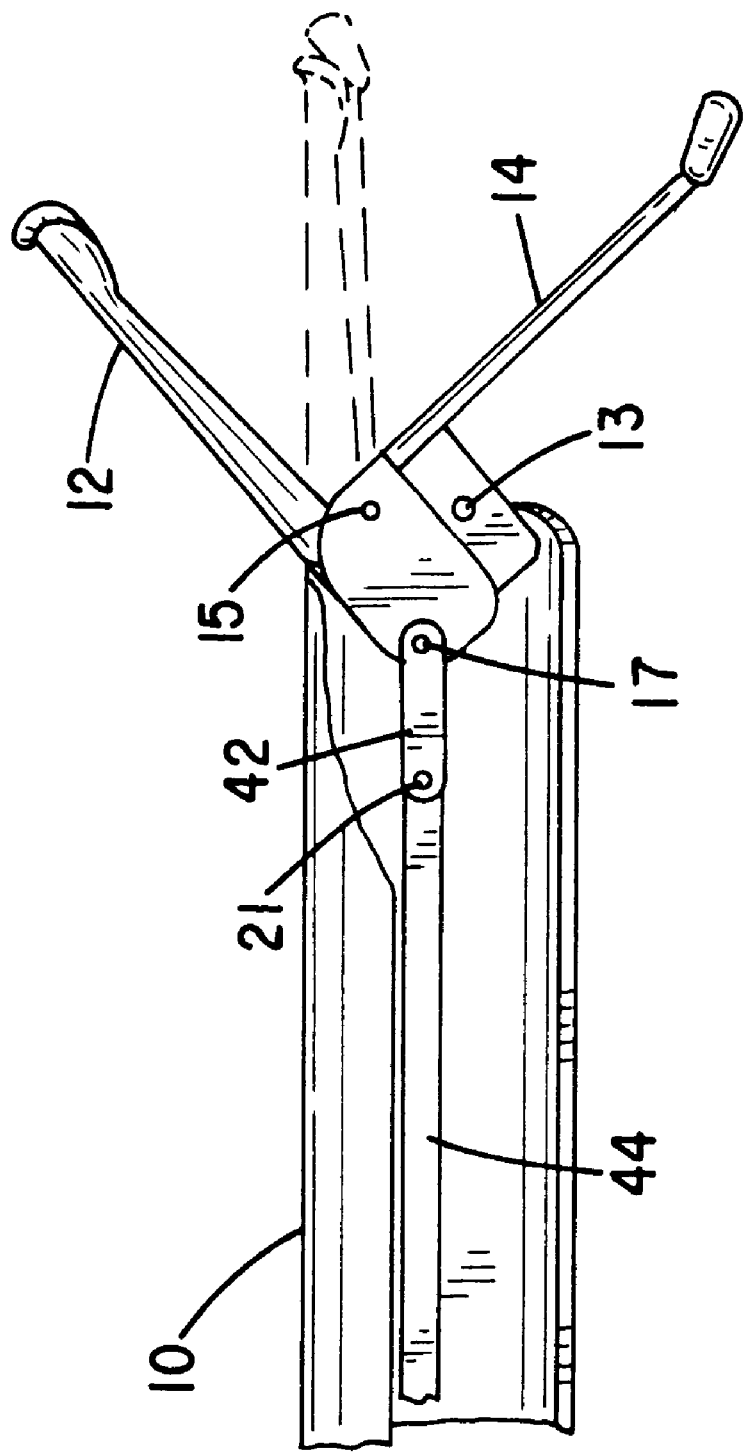
FIG. 19. is a right-side cross sectional view of the laryngoscope blade with both the upper and lower blade tips attached and activated.

The upper blade tip 12 is illustrated in FIGS. 7, 8 and 9. The upper blade tip 12 is pivotally secured to the upper tip flange 38 at pivot connection 13 by hinge pin 41 and to the blade 10 at pivot connection 45. This is illustrated in FIGS. 6, 10 and 18. The lower blade tip 14 is illustrated in FIGS. 13, 14 and 15. The lower blade tip 14 is pivotally secured to the lower tip flange 36 at pivot connection 15 by hinge pin 39. This is illustrated in FIGS. 6 and 18. When the laryngoscope is in the inactive or neutral position the distal end of the lower blade tip 14 is received around the distal end of the upper blade tip 12 as illustrated in FIG. 18. This allows for easy insertion of the blade 10 in the patient's oral cavity A and laryngopharynx B. When the laryngoscope is activated the distal end of the upper blade tip 12 moves away from the distal end of the lower blade tip 14 about its pivot connection 13 and the distal end of lower blade tip 14 moves away from the distal end of upper blade tip 12 about its pivot connection 15. This is illustrated in FIG. 19.

Figure 29:
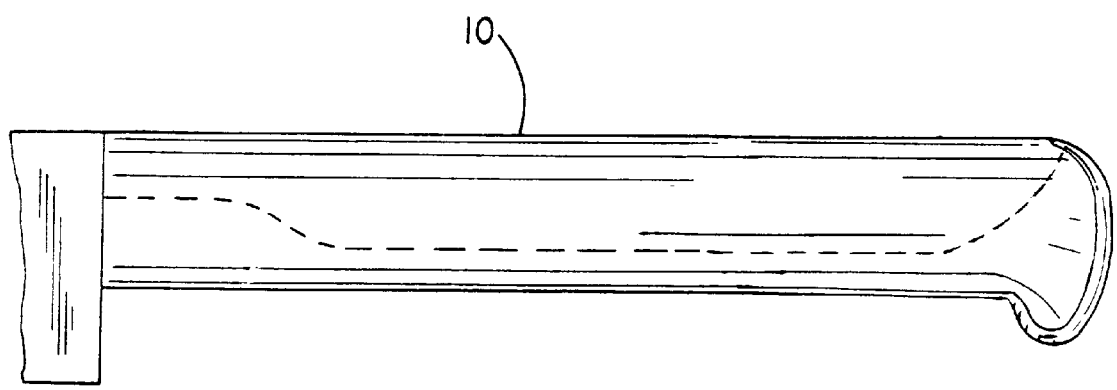
FIG. 29 is a top-elevational view of the laryngoscope blade with the width of its distal end flared beyond the width of the rest of the blade.

As illustrated in FIG. 18, the width of the upper blade tip 12 and the width of the lower blade tip 14 flare out beyond the width of the blade 10. This design gives the tips more surface area to spread apart a patient's throat tissue and to stabilize the epiglottis D while displacing it anteriorly. This design also allows the blade 10 itself to be narrower which gives the laryngoscope greater maneuverability and provides the operator with greater exposure of the throat structure. This feature can also be incorporated into a blade without movable blade tips (12 and 14) as illustrated in FIG. 29.

Figure 25:
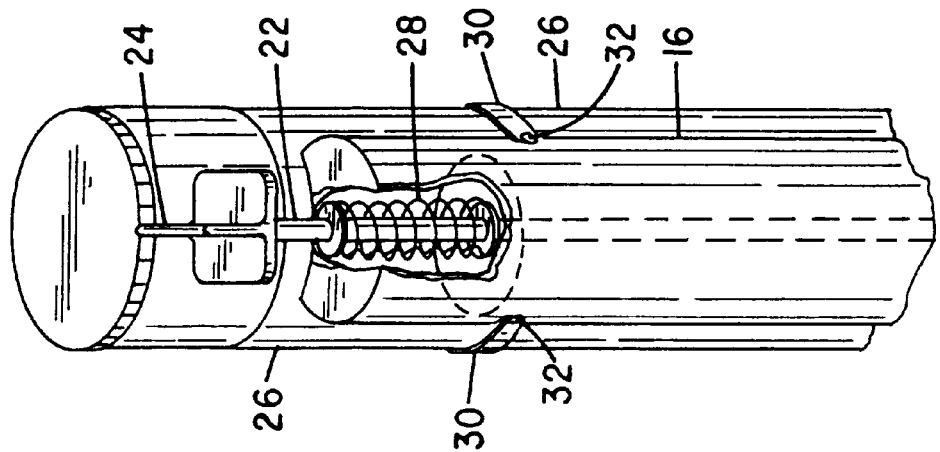
FIG. 25 is a right cross-sectional view of the biasing spring.

To use the laryngoscope the operator grasps the handle 26 and inserts his or her thumb between the thumb strap 30 and the thumb plunger 20. Once the blade 10 is optimally positioned in the patient's laryngopharynx B the operator asserts pressure with his or her thumb on the thumb plunger 20 to spread the tips apart. The thumb plunger 20 is illustrated in FIG. 24. The thumb plunger 20 is solidly connected to the thumb push rod 22. The thumb push rod 22 is encased in the thumb push rod guide 16 as illustrated in FIG. 24. When pressure is asserted on the thumb plunger 20, the thumb push rod 22 is moved downward. A biasing spring 28, asserts pressure in the opposite direction thereby returning the thumb push rod 22 and blade tips (12 and 14) to their neutral position when no pressure is asserted on the thumb plunger 20. The biasing spring 28 is illustrated in FIG. 25.

An important feature of the design of my invention is that the mechanism that activates the blade tips (12 and 14) is a direct mechanism. Therefore, even if the biasing spring 28 failed, the operator would still be able to return the tips to their neutral position by asserting upward pressure on the thumb strap 24 with his or her thumb. The thumb strap 24 also provides the operator with precise control over the movement of the blade tips (12 and 14). The thumb strap 24 is illustrated in FIG. 24.

Figure 20:
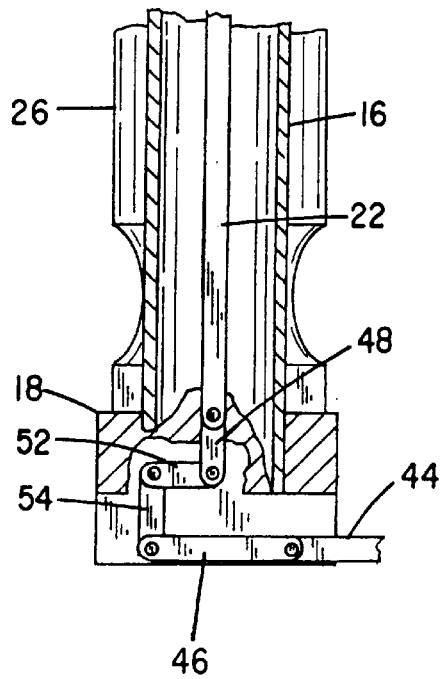
FIG. 20. is a right-side cross-sectional view of the thumb push rod housing and blade body base showing the connections of the activating mechanism.
Figure 21:
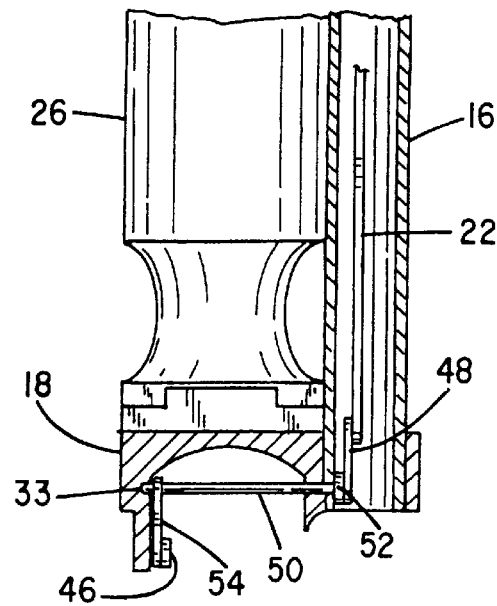
FIG. 21 is a back cross-sectional view of the thumb push rod and blade body base further showing the connections of the activating mechanism seen in FIG. 20.
Figure 22:
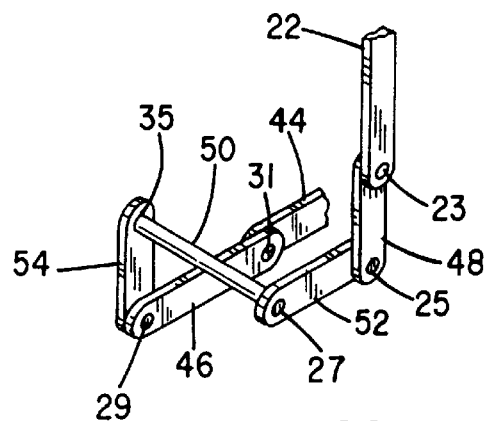
FIG. 22 is a perspective view of the activating mechanism shown in FIG. 20 and FIG. 21.

The activation mechanism is illustrated in FIGS. 20, 21 and 22. The activation mechanism converts vertical movement of the thumb push rod 22 into horizontal movement of the blade push rod 44. One end of the blade push rod 22 is pivotally connected to one end of the thumb push rod link 48 by pivot 23. The other end of the thumb push rod link 48 is pivotally connected to the horizontal push rod link 52 by pivot 25. The other end of the horizontal push rod link 52 is solidly connected to the torque rod 50 about connection 27. The other end of the torque rod 50 extends through the vertical blade rod link 54 at connection 35. This is also a solid connection. The part of the torque rod 50 extending through the vertical blade rod link 54 is received in cavity 33 so as to stabilize the activating mechanism. In addition, the diameter of cavity 33 is slightly larger than the diameter of the torque rod 50 so as to allow the torque rod 50 to freely rotate. The other end of the vertical blade rod link 54 is pivotally connected to the blade rod link 46 by pivot 29. The other end of the blade rod link 46 is pivotally connected to the blade push rod 44 by pivot 31.

Figure 17:
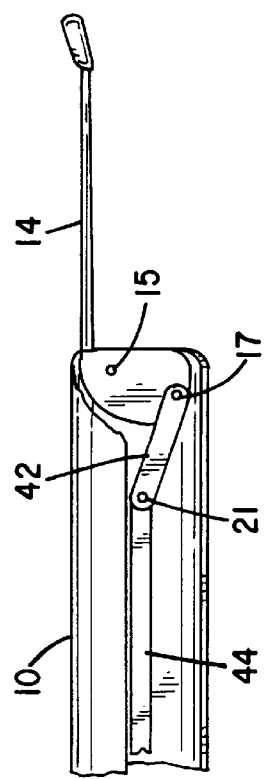
FIG. 17 is a right-side cross-sectional view of the laryngoscope blade with the lower blade tip attached showing the pivot connections.
Figure 16:
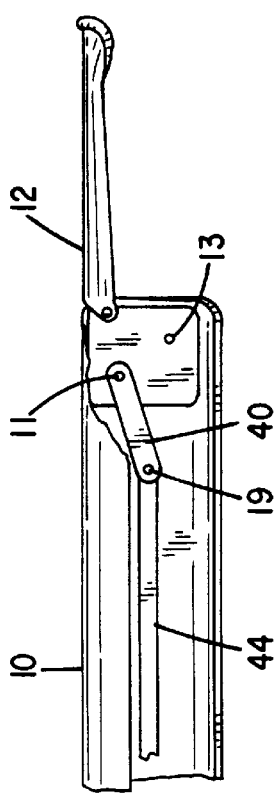
FIG. 16 is a right-side cross-sectional view of the laryngoscope blade with the upper tip attached showing the pivot connections.

As illustrated in FIGS. 16 and 17, the other end of the blade push rod 44 is pivotally connected to the upper tip link 40 by pivot 19 and the lower tip link 42 by pivot 21. The other end of the upper tip link 40 is pivotally connected to the upper blade tip 12 by pivot 11. The other end of the lower tip link 42 is pivotally connected to the lower blade tip 14 by pivot 17.

Figure 28:
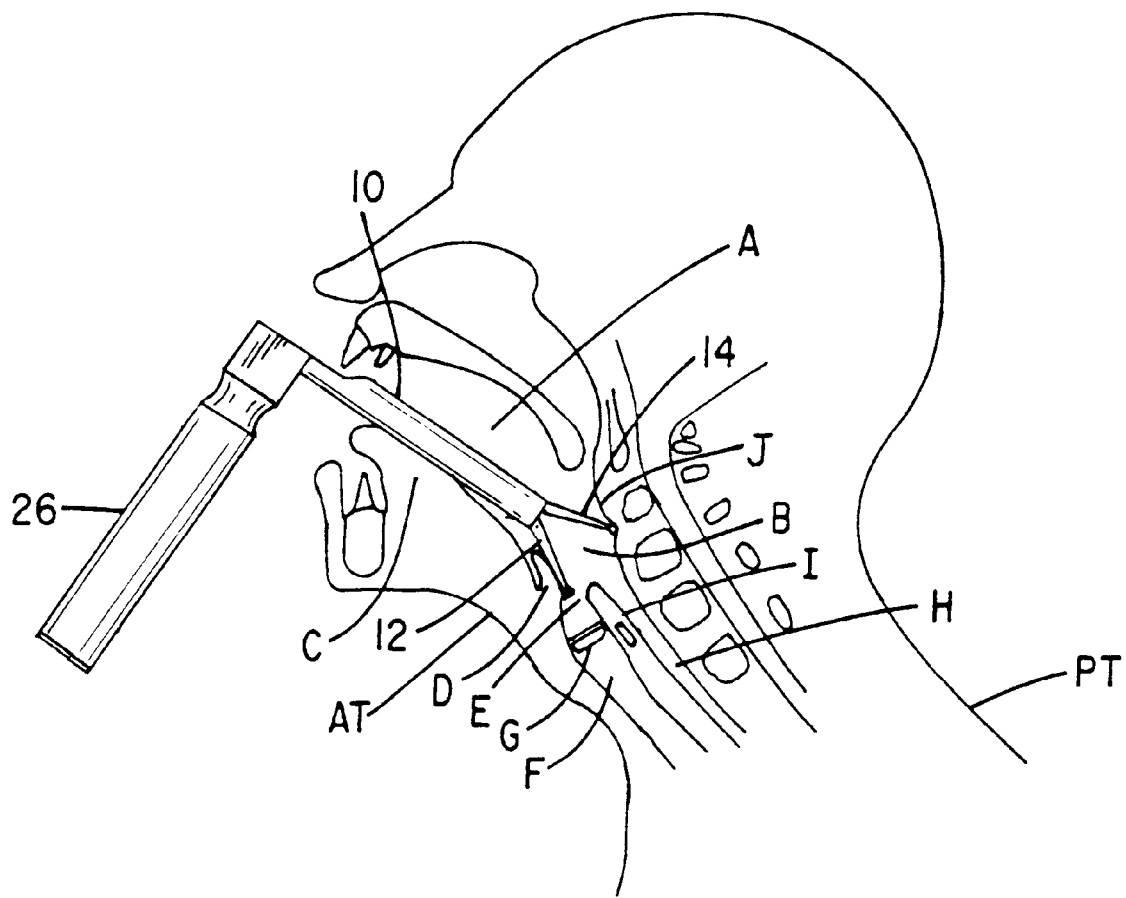
FIG. 28 is a schematic sketch of a section of a human head with the laryngoscope blade of FIG. 1 inserted and activated.

My laryngoscope invention in use is illustrated in FIG. 28 in association with a patient undergoing endotracheal intubation. The patient is shown having an oral cavity A, a laryngopharynx B, a tongue C, an epiglottis D, vocal cords G, aditus of larynx E, trachea F, cricoid cartilage ring I (note: only posterior portion of the cricoid cartilage ring is shown, the entire cricoid cartiledge extends anteriorly around the trachea 360 degrees), an esophagus H and a posterior wall of laryngopharynx J. FIG. 28 also illustrates the anterior AT and posterior PT sides of the patient. During a difficult intubation, the aditus of larynx E and the vocal cords G may be anterior AT. When the blade tips (12 and 14) are activated the upper blade tip 12 pushes the epiglottis anteriorly AT and the lower blade tip 14 pushes the posterior wall of laryngopharynx posteriorly PT spreading apart the patient's throat tissue. Moreover, the pressure asserted by the lower blade 14 on the posterior wall of laryngopharynx J provides stability to the upper blade tip 12, thereby allowing greater anterior displacement of the upper blade tip 12 without rotation of the blade 10.

In addition, my invention will enhance the outcome if "Sellick's Maneuver or Criciod Pressure" is used on a patient. Sellick's Manuver is a procedure used to inhibit reflux of gastric contents by applying posterior PT pressure to the cricoid cartilage ring I of the trachea F, thereby compressing the patient's esophagus H. This procedure also facilitates visualization of the aditus of larynx E by pushing the entire laryngal structures (E, F, G, I) posteriorly PT and allows the prying movement of the blade tips (12 and 14) to be more effective by stabilizing anterior movement of the entire laryngal structures (E, F, G, I). The outcome of the pressure asserted by the blade tips (12 and 14), whether Criciod Pressure is asserted or not, is that the aditus of larynx E and vocal cords G are exposed quickly and effectively so intubation can be achieved.

My invention may be made of metal or plastic commonly used for medical devices but I do not limit myself to any particular type of material. Although, alternative embodiments and modifications are contemplated, I have disclosed my preferred embodiment. Changes and alterations may be made to my preferred embodiment without departing from the spirit of and scope of my invention, as defined by the following claims.

What is claimed is:

1. A laryngoscope comprising:

a handle of a given length;

a blade adapted to be inserted into a patient's oral cavity having a proximal end and a distal end, the blade having an upper plate and an edge plate for displacing a tongue of a patient, the upper plate having opposing sides, the edge plate extending substantially at a right angle from a side of the upper plate forming a viewing channel, the proximal end of the blade being connected to one end of the handle at a substantially right angle adjacent the upper plate of the blade;

a light source connected to the distal end of the blade;

a upper blade tip having a proximal end and a distal end, the proximal end being pivotally connected to the distal end of the blade;

a lower blade tip having a proximal end and a distal end, the proximal end being pivotally connected to the distal end of the blade and being received under the upper blade tip; and a thumb activation means for rotating the distal ends of the blade tips away from each other about their pivot connections whereby once the laryngoscope blade is inserted in a patient's laryngopharynx and activated the blade tips spread apart the throat tissue exposing the aditus of larynx so an intubation tube can be quickly and efficiently inserted.

2. A laryngoscope as set forth in claim 1, wherein the handle is solidly connected to the blade.

3. A laryngoscope as set forth in claim 1, wherein the handle is detachably connected to the blade.

4. A laryngoscope as set forth in claim 1, wherein the blade, the upper blade tip, and lower I claim blade tip are substantially straight throughout there respective lengths.

5. A laryngoscope as set forth in claim 1, wherein the blade, the upper blade tip and the lower blade tip are curved with respect to their lengths.

6. A laryngoscope as set forth in claim 1, wherein the blade further having a cutout section for providing added room to maneuver the laryngoscope in relation to a patent's upper teeth, the cutout section being positioned adjacent the proximal end of the blade, adjacent the edge plate of the blade and opposite the upper plate of the blade; and the edge plate of the blade having a height, the height of the edge plate being tapered shorter by the cutout portion of the blade.

7. A laryngoscope as set forth in claim 1, wherein the height of the edge plate of the blade remains substantially constant throughout its length.

8. A laryngoscope as set forth in claim 1, wherein the upper plate of the blade and the upper blade tip each have a given width, the width of the distal end of the upper blade tip being flared beyond the width of the upper plate of the blade from a side of the upper plate that is opposite the side of the upper plate that the edge plate extends from whereby the added surface area of the flared distal end of the upper blade tip allows the blade to be made narrower for providing added maneuverability of the laryngoscope.

9. A laryngoscope as set forth in claim 1, wherein the upper plate of the blade and the lower blade tip each have a given width, the width of the distal end of the lower blade tip being flared beyond the width of the upper plate of the blade from a side of the upper plate that is opposite the side of the upper plate that the edge plate extends from, whereby the added surface area of the flared distal end of the lower blade tip allows the blade to be made narrower for providing added maneuverability of the laryngoscope.

10. A laryngoscope as set forth in claim 1 further comprising:

a thumb strap of a given length for engaging a human thumb, the thumb strap having a first end and a second end;

a thumb plunger having a first end surface for manually applying pressure by an operator's thumb and a second end surface, the thumb plunger being positioned adjacent to the handle for thumb activation, the first and second ends of the thumb strap being connected to the first end surface of the thumb plunger in a manner that creates an enclosed semi-loop slightly larger than a human thumb;

a thumb push rod of a given length and diameter being positioned adjacent to the handle and being substantially parallel to the handle, the thumb push rod having one end connected to the second end surface of the thumb plunger; and a blade push rod of a given length being positioned adjacent to the blade and being substantially parallel to the blade, one end of the blade push rod being operatively associated with the thumb push rod, the other end of blade rod being operatively associated with upper and lower blade tips whereby pressure exerted by an operator's thumb on the thumb plunger activates the distal tips spreading apart the patient's throat tissue.

11. A laryngoscope as set forth in claim 10 further comprising:

a thumb push rod guide having a length shorter than the length of the thumb push rod, the thumb push rod guide being shaped to form an enclosed surface area, one end of the thumb push rod guide having an opening slightly larger in diameter than the diameter of the thumb push rod, the thumb push rod being received in the thumb push rod guide wherein a portion of the thumb push rod extends through the opening in the thumb push rod guide; and a biasing spring having a diameter, the diameter of the biasing spring being slightly larger than the diameter of the thumb push rod, the biasing spring being received inside the thumb push rod guide and around the thumb push rod, one portion of the spring being engaged with the thumb push rod and another portion being engaged with the thumb push rod guide in a manner to cause pressure to be asserted on the thumb push rod.

12. A laryngoscope as set forth in 11 further comprising:

a pair of stabilizing knobs being connected to the thumb push rod guide;

a stabilizing strap having a length, the stabilizing strap being adapted to fit around a standard laryngoscope handle, the ends of the stabilizing strap being detachably connected to the stabilizing knobs.

13. A laryngoscope comprising:

a handle of a given length;

a blade being adapted to be inserted into a patient's throat cavity having a proximal end and a distal end, the blade also having an upper plate and a edge plate, the upper plate having opposing sides, the edge portion extending substantially at a right angle from a side of the upper plate, the proximal end of the blade being connected to one end of the handle at a substantially right angle adjacent the upper plate of the blade;

the blade further having a cutout section for providing added room to maneuver the laryngoscope in relation to a patent's upper teeth when in use, the cutout section being positioned adjacent the proximal end of the blade, adjacent the edge plate of the blade and opposite the upper plate of the blade;

the edge portion of the blade having a height, the height of the edge portion being tapered shorter by the cutout portion of the blade; and a light source connected to the distal end of the blade.

14. A laryngoscope as set forth in claim 13, wherein the handle is solidly connected to the blade.

15. A laryngoscope as set forth in claim 13, wherein the handle is detachably connected to the blade.

16. A laryngoscope as set forth in claim 13, wherein the blade is substantially straight throughout its length.

17. A laryngoscope as set forth in claim 13, wherein the blade is curved with respect to its length.

18. A laryngoscope comprising:

a handle of a given length;

a blade adapted to be inserted into a patient's throat cavity, the blade having a proximal end and a distal end, the blade further having a upper plate and an edge plate for displacing a tongue of a patient, the upper plate having opposing sides, the edge plate extending substantially at a right angle from a side of the upper plate, the proximal end being connected to one end of the handle in substantially a right angle adjacent the upper plate of the blade;

the upper plate of the blade having a width, the width of the distal end of the upper plate being flared wider than the width of the rest of the upper plate from a side of the upper plate that is opposite the side of the upper plate that the edge plate extends from, whereby the added surface area at the distal end of the blade allows the rest of the blade to be made narrower for providing added maneuverability of the laryngoscope; and a light source connected to the distal end of the blade.

19. A laryngoscope as set forth in claim 18, wherein the handle is solidly connected to the blade.

20. A laryngoscope as set forth in claim 18, wherein the handle is detachably connected to the blade.

21. A laryngoscope as set forth in claim 18, wherein the blade is substantially straight throughout its length.

22. A laryngoscope as set forth in claim 18, wherein the blade is curved with respect to its length.

* * * * *